United States Patent [19]

Ohki et al.

[11] 4,439,519
[45] Mar. 27, 1984

[54] SILVER-HALIDE PHOTOGRAPHIC LIGHT-SENSITIVE MATERIAL

[75] Inventors: Nobutaka Ohki; Ken Kawata; Isamu Itoh, all of Minami-ashigara, Japan

[73] Assignee: Fuji Photo Film Co., Ltd., Kanagawa, Japan

[21] Appl. No.: 491,829

[22] Filed: May 5, 1983

[30] Foreign Application Priority Data

May 6, 1982 [JP] Japan ................................ 57-75807

[51] Int. Cl.³ .............................................. G03C 7/30
[52] U.S. Cl. .................................... 430/405; 430/442; 430/467; 430/484; 430/955; 430/959; 430/566
[58] Field of Search ............... 430/566, 380, 405, 442, 430/467, 484, 959, 955

[56] References Cited

U.S. PATENT DOCUMENTS 4,060,418 11/1977 Waxman et al. .................... 430/484

Primary Examiner—Mary F. Downey
Attorney, Agent, or Firm—Sughrue, Mion, Zinn, Macpeak and Seas

[57] ABSTRACT

A silver halide photographic light-sensitive material containing a diffusion resistant coupler, a light-sensitive silver halide and at least one compound represented by the following general formula (I) in the same layer or different layers on a support.

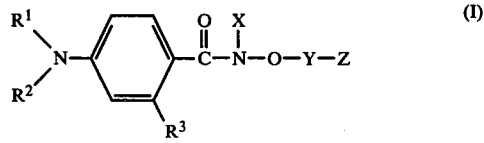

wherein $R^1$ and $R^2$ independently represent an alkyl group having from 1 to 5 carbon atoms, a hydroxyalkyl group having from 1 to 5 carbon atoms, an alkoxyalkyl group having from 2 to 10 carbon atoms or an alkylsulfonamidoalkyl group having from 2 to 10 carbon atoms; $R^3$ represents a hydrogen atom, an alkyl group having from 1 to 5 carbon atoms or an alkoxy group having from 1 to 5 carbon atoms; X represents a hydrogen atom or a group capable of being removed with alkali; Y represents

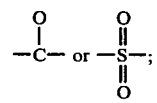

and Z represents an alkyl group, an alkenyl group, an aryl group or a heterocyclic group.

The compound represented by the general formula (I) is a novel precursor of a color developing agent which provides a sufficiently high color density on development and causes less desensitization as well as less fog or stain formation during storage of any photographic light-sensitive material containing it. A method of forming a color photographic image using the silver photographic light-sensitive material is also disclosed.

18 Claims, No Drawings

SILVER-HALIDE PHOTOGRAPHIC LIGHT-SENSITIVE MATERIAL

FIELD OF THE INVENTION

The present invention relates to a photographic light-sensitive material. More particularly, the present invention relates to a precursor of a color developing agent and a silver halide photographic light-sensitive material containing the precursor.

BACKGROUND OF THE INVENTION

A general process for forming a color image with a photographic light-sensitive material such as a color photographic light-sensitive material comprises developing a silver halide photographic light-sensitive material using an aromatic primary amine developing agent in the presence of a color coupler having the ability to form a dye by reacting with an oxidation product of the developing agent to form an azomethine dye or an indoaniline dye. This color development process which was invented originally by L. D. Mannes and L. Godowsky in 1935 and improved upon is now widely used all over the world in the photographic field.

The processing of color photographic light-sensitive materials essentially comprises the following three steps:

(1) a color development step,
(2) a bleaching step,
(3) a fixing step.

The bleaching step and the fixing step may be carried out at the same time. Namely, a bleach-fixing step (the so-called blix step), by which developed silver and undeveloped silver halide are removed can be used. In actual development processing, auxiliary steps for maintaining the photographic or physical quality of the images formed or the improving the storage stability of the images, etc. are employed in addition to the above described two essential steps consisting of color development and silver-removal. For example, steps using a bath such as a hardening bath for preventing an excessive softening of the light-sensitive layers during processing, a stopping bath for effectively stopping the development reaction, a stabilizing bath for stabilizing the images formed or a defilming bath for removing a backing layer on the support can be employed.

Usually, an aromatic primary amine developing agent is dissolved in an aqueous alkaline solution and used as a color developing solution. If the aromatic primary amine developing agent is incorporated in the light-sensitive material, the development can be essentially carried out using only an aqueous alkaline solution. Consequently, the developing solution can be easily prepared and it is possible to minimize any change in the composition of the developing solution, so that control of the developing solution can be easily carried out. Further, there are many advantages, such as marked decrease in the BOD of the waste liquor and easy treatment of the waste liquor. However, in general, the incorporation of an aromatic primary amine developing agent into a light-sensitive material has not presently been utilized in practice. Problems preventing such utilization include desensitization of the light-sensitive material and occurrence of fogs or stains during storage, or insufficient color formation in the processing.

A black-and-white developing agent such as hydroquinone or catechol, etc. can be incorporated into the light-sensitive material in a comparatively stable state. For example, U.S. Pat. No. 3,295,978 discloses that such a developing agent can be incorporated into the light-sensitive material as a metal complex salt. On the contrary, it is difficult to incorporate aromatic primary amine developing agents into light-sensitive materials in a stable manner because of their lack of stability.

Several methods for incorporating an aromatic primary amine developing agent into a light-sensitive material are known. For example, U.S. Pat. No. 3,342,599 describes the use of a Schiff base of an aromatic primary amine developing agent with salicylaldehyde as a precursor of a developing agent. U.S. Pat. No. 3,719,492 discloses the use of a combination of a metal salt such as a lead or cadmium salt with an aromatic primary amine developing agent. In British Pat. No. 1,069,061, a phthalimide type precursor prepared by reacting an aromatic primary amine with phthalic acid is used. Other known methods are described in German Pat. Nos. 1,159,758 and 1,200,679, U.S. Pat. No. 3,705,035, etc. However, the requirements of sufficient color density formation on development, a lack of desensitization and the elimination of fog or stains on storage of the light-sensitive material can not be obtained using any of these prior art techniques.

SUMMARY OF THE INVENTION

An object of the present invention is to provide a precursor of a developing agent which provides a sufficiently high color density on development and substantially prevents desensitization and the formation of fog or stains during storage.

Another object of the present invention is to provide a technique for incorporating a precursor of an aromatic primary amine developing agent into a light-sensitive material, which results in a sufficiently high color density on development, less desensitization and little occurrence of fog or stains during storage of the light-sensitive material even though a precursor of an aromatic primary amine developing agent is incorporated into the light-sensitive material.

Other objects of the present invention will be apparent from the following detailed description and examples.

The objects of the present invention can be attained by a precursor of a developing agent represented by the general formula described below, and a silver halide photographic light-sensitive material containing a diffusion resistant coupler, a light-sensitive silver halide and at least one compound represented by the following general formula (I) in the same layer or different layers on a support.

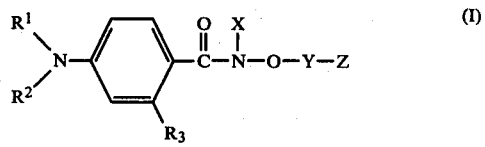

wherein $R^1$ and $R^2$, independently represent an alkyl group having from 1 to 5 carbon atoms, a hydroxyalkyl group having from 1 to 5 carbon atoms, an alkoxyalkyl group having from 2 to 10 carbon atoms or an alkylsulfonamidoalkyl group having from 2 to 10 carbon atoms; $R^3$ represents a hydrogen atom, an alkyl group having from 1 to 5 carbon atoms or an alkoxy group having from 1 to 5 carbon atoms; X represents a hydrogen atom or a group capable of being removed with alkali; Y represents

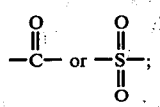

and Z represents an alkyl group, an alkenyl group, an aryl group or a heterocyclic group.

DETAILED DESCRIPTION OF THE INVENTION

Specific examples of the groups represented by $R^1$ and $R^2$ in the general formula (I) include a methyl group, an ethyl group, a propyl group, a butyl group, a hydroxyethyl group, a hydroxypropyl group, a methoxyethyl group, an ethoxyethyl group, a methylsulfonamidoethyl group, etc., with a methyl group, an ethyl group, a propyl group, a butyl group, a hydroxypropyl group, a methylsulfonamidoethyl group being preferred.

Specific examples of the groups represented by $R^3$ in the general formula (I) include a methyl group, an ethyl group, a butyl group, a methoxy group, an ethoxy group, etc., with a methyl group being preferred.

Examples of X in the general formula (I) include, in addition to a hydrogen atom, an alkylcarbonyl group (preferably having up to 5 carbon atoms) or

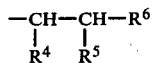

(wherein $R^4$ and $R^5$ independently represent a hydrogen atom or an alkyl group, for example, a methyl group, an ethyl group, etc.; and $R^6$ represents an electron attracting group, for example, a cyano group or a methanesulfonyl group, etc.), Specific examples of the groups represented by X include a a hydrogen atom, —COCH$_3$, —COCH$_2$Cl, —COCF$_3$, —CH$_2$CH$_2$CN, etc., with a hydrogen atom being preferred.

Preferred examples of Z in the general formula (I) include an alkyl group having from 1 to 10 carbon atoms, an alkenyl group having from 2 to 10 carbon atoms, an aryl group having from 6 to 10 carbon atoms and a heterocyclic group having from 1 to 10 carbon atoms. The groups may be further substituted with an alkyl group having 1 to 30 carbon atoms, a cycloalkyl group having 3 to 30 carbon atoms, an alkoxy group having 1 to 30 carbon atoms, an aryl group having 6 to 30 carbon atoms, an aryloxy group having 6 to 30 carbon atoms, a halogen atom, a carbamoyl group having 1 to 30 carbon atoms, a sulfamoyl group having 1 to 30 carbon atoms, an amido group having 1 to 30 carbon atoms, an alkylthio group having 1 to 30 carbon atoms, an arylthio group having 6 to 30 carbon atoms, a hydroxy group, an amino group having 0 to 30 carbon atoms, an acyl group having 1 to 30 carbon atoms, etc.

Specific examples of the groups represented by Z include a methyl group, a chloromethyl group, a dichloromethyl group, a phenoxymethyl group, etc. for the alkyl group; a vinyl group, a 1-methylvinyl group, a 2-chlorovinyl group, an allyl group, etc. for the alkenyl group; a 3,4-dichlorophenyl group, a 3,5-dinitrophenyl group, a 3,6-dihydroxy-2,4-dimethylphenyl group, a 2,5-dihydroxy-4-pentadecylphenyl group, etc. for the aryl group; a 3-pyridyl group, a 2-furyl group, etc. for the heterocyclic group, but they are not limited thereto. Of these, the alkyl and aryl compounds are preferred.

Examples of preferred compounds of the precursors represented by the above described general formula (I) include precursors of aromatic primary amine developing agents wherein $R^2$ and $R^3$ independently represent an alkyl group having from 1 to 5 carbon atoms.

Also, examples of preferred compounds of the precursors represented by the above described general formula (I) include precursors of aromatic primary amine developing agents wherein Y represents

Further, examples of preferred compounds of the precursors represented by the above described general formula (I) include precursors of aromatic primary amine developing agents wherein Z represents a substituted or unsubstituted alkyl group or a substituted or unsubstituted aryl group.

Moreover, examples of preferred compounds of the precursors represented by the above described general formula (I) include precursors of aromatic primary amine developing agents wherein Z represents a substituted or unsubstituted dihydroxybenzene, a substituted or unsubstituted dihydroxynaphthalene, a substituted or unsubstituted aminophenol or a substituted or unsubstituted aminonaphthol.

The precursor of an aromatic primary amine developing agent represented by the general formula (I) described above is a compound of a hydroxamic acid ester type which forms a compound of a paraphenylenediamine type, i.e., an aromatic primary amine developing agent by bringing it into contact with an alkaline processing solution. This indicates that the bonding between the carbon atom at the ortho position to $R^3$ in the benzene ring and the carbon atom of the carbonyl group is converted to the bonding between the carbon atoms and a nitrogen atom, that is, a rearrangement reaction occurs. Among known precursors of aromatic primary amine developing agents, none form a developing agent by a rearrangement reaction. Therefore, the precursors of aromatic primary amine developing agents of a hydroxamic acid ester type according to the present invention belong to a novel class of compounds.

Specific examples of compounds represented by the general formula (I) above which can be used in the present invention are described below. However, the present invention is not to be construed as being limited only to these compounds.

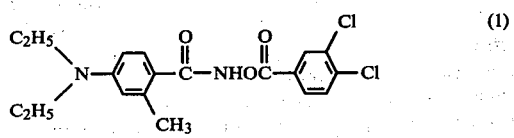

(1)

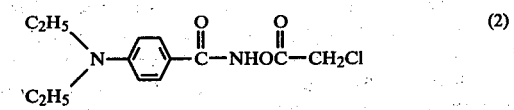

(2)

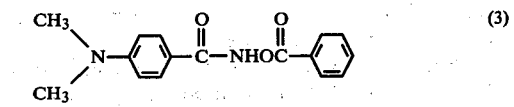

(3)

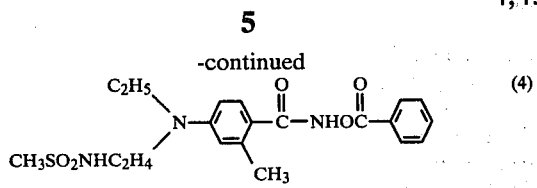
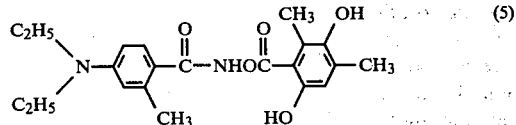
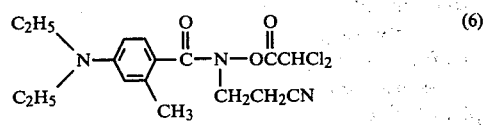
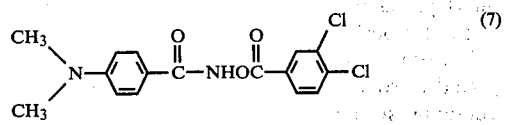
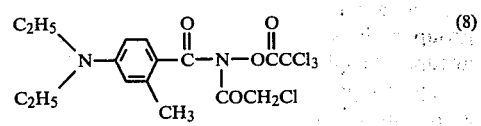
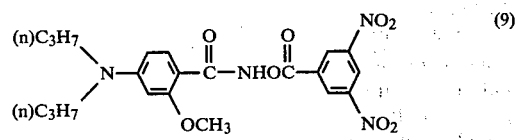
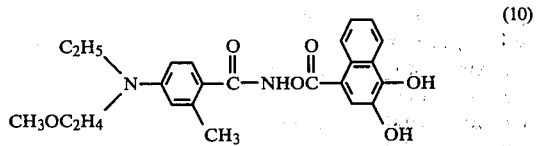
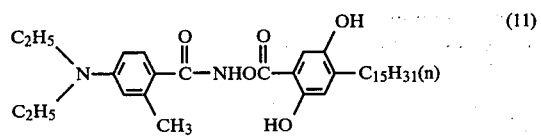
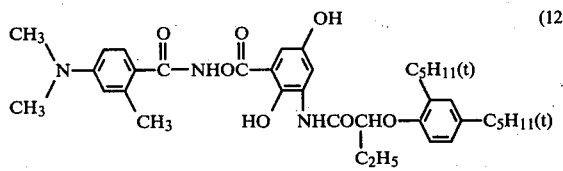
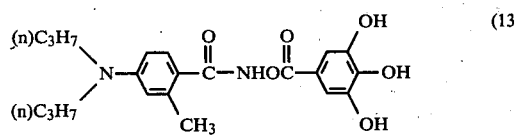
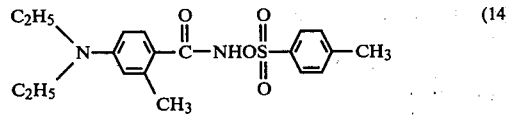
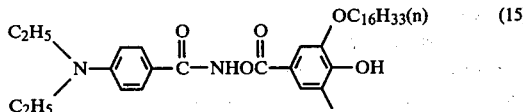

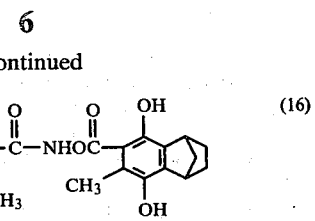
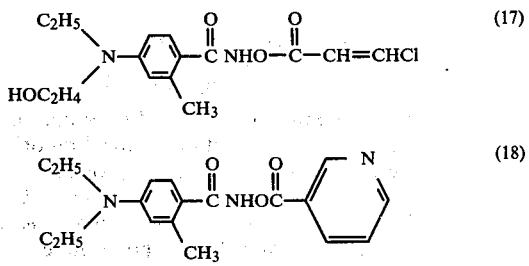

Of the above compounds, Compounds 1 to 5, 7, 9–13, 15 and 16 are preferred.

The compounds represented by the general formula (I) can be synthesized using or referring to the methods described below.

SYNTHESIS EXAMPLE 1

Synthesis of 4-Dimethylaminobenzohydroxamic acid 23 g of 4-dimethylaminobenzoic acid was dissolved in 200 ml of methanol to which was added 2 ml of concentrated sulfuric acid and the mixture was refluxed with heating for 2 days. After cooling, the reaction mixture was poured into an aqueous solution of sodium bicarbonate and the crystals thus deposited were collected by filtration, washed with water and dried to obtain 24 g of 4-dimethylaminobenzoic acid methyl ester having a melting point of 101° to 102° C.

7.4 g of hydroxylamine hydrochloride was dissolved in 200 ml of water to which was added dropwise 106 ml of 1 N aqueous solution of sodium hydroxide while cooling. The resulting mixture was added with stirring to 300 ml of a tetrahydrofuran solution containing 9.0 g of 4-dimethylaminobenzoic acid methyl ester dissolved at room temperature. After stirring for 8 hours, 5 ml of 1 N aqueous solution of sodium hydroxide was added thereto and the mixture was further stirred for 3 days. After adjusting the pH of the resulting mixture between 4 and 5 by adding a diluted aqueous hydrochloric acid solution, the mixture was extracted with ethyl acetate and the extract was dried with sodium sulfate and concentrated. The resulting crystals were recrystallized from acetonitrile to obtain 4 g of the desired compound having a melting point of 162° to 163° C. The structure of the compound was confirmed using mass spectrum and NMR spectrum, etc.

Elemental Analysis for $C_9H_{12}N_2O_2$: Calculated (%); C: 59.99%; H: 6.71%; N: 15.54%. Found (%); C: 59.96%; H: 6.71%; N: 15.35%.

SYNTHESIS EXAMPLE 2

Synthesis of Compound (3)

0.9 g of 4-dimethylaminobenzohydroxamic acid was dissolved in 50 ml of acetonitrile to which were added dropwise in order 0.4 ml of pyridine and 10 ml of an acetonitrile solution containing 0.7 g of benzoyl chloride with stirring at room temperature. After the completion of the addition, the mixture was further stirred for 30 minutes and then poured into 300 ml of water.

The crystals thus deposited were collected by filtration and recrystallized from ethanol to obtain 1.1 g of the desired compound having a melting point of 160° to 161° C. The structure of the compound was confirmed using mass spectrum and NMR spectrum, etc.

Elemental Analysis for $C_{16}H_{16}N_2O_3$: Calculated(%); C: 67.59%; H: 5.67%; N: 9.85%. Found(%); C: 67.44%; H: 5.48%; N: 9.81%.

SYNTHESIS EXAMPLE 3

Synthesis of Compound (7)

In the same procedure as described in Synthesis Example 2 using 1.0 g of 3,4-dichlorobenzoyl chloride in place of 0.7 g of benzoyl chloride, 1.3 g of the desired compound having a melting point of 151° to 152° C. was obtained. The structure of the compound was confirmed using mass spectrum, NMR spectrum, etc.

Elemental Analysis for $C_{16}H_{14}Cl_2N_2O_3$: Calculated(%); C: 54.41; H: 3.99; N: 7.93. Found(%); C: 54.62; H: 4.12; N: 7.89.

SYNTHESIS EXAMPLE 4

Synthesis of 4-diethylamino-2-methylbenzonitrile

The desired compound was obtained as an oily product in accordance with the method described in *J. Org. Chem.*, Vol. 27, page 4372 (1962) using 4-diethylamino-2-methylbenzaldehyde as a strating material. The structure of the compound was confirmed using IR spectrum and mass spectrum, etc.

Elemental Analysis for $C_{12}H_{16}N_2$: Calculated(%); C: 76.55; H: 8.57; N: 14.88. Found(%); C: 76.42; H: 8.54; N: 14.92.

SYNTHESIS EXAMPLE 5

Synthesis of 4-diethylamino-2-methylbenzoic acid 19 g of 4-diethylamino-2-methylbenzonitrile was dissolved in a mixture of 50 ml of concentrated sulfuric acid and 50 ml of water and the solution was heated on a water bath for 3 days. The resulting mixture was neutralized and extracted with ethyl acetate. Then the residue was extracted with 300 ml of water containing 8 g of sodium hydroxide dissolved and to the aqueous extract was added dropwise 17 ml of concentrated sulfuric acid with stirring. The crystals thus deposited were collected by filtration and dried to obtain 12 g of the desired compound having a melting point of 148° to 150° C. The structure of the compound was confirmed using mass spectrum and NMR spectrum, etc.

Elemental Analysis for $C_{12}H_{17}NO_2$: Calculated(%); C: 69.53; H: 8.27; N: 6.76. Found(%); C: 69.46; H: 8.03; N: 6.53.

SYNTHESIS EXAMPLE 6

Synthesis of Compound (1)

In the same procedure as described in Synthesis Example 1 and then Synthesis Example 3 using 29 g of 4-diethylamino-2-methylbenzoic acid as a strating material in place of 23 g of 4-dimethylaminobenzoic acid, 1.5 g of the desired compound was obtained. The structure of the compound was confirmed using mass spectrum and NMR spectrum, etc.

Elemental Analysis for $C_{19}H_{20}Cl_2N_2O_3$: Calculated(%); C: 57.73; H: 5.10; N: 7.09. Found(%); C: 57.85; H: 5.16; N: 6.92.

Other compounds on general formula (I) can be synthesized in the same manner as described above or the methods as described in *J.A.C.S.*, Vol. 59, page 2308 (1937), ibid., Vol. 61, page 618 (1939), and *Chem. Rev.*, Vol. 33, page 209 (1942).

The compound represented by the general formula (I) above may be dispersed in a hydrophilic colloid solution directly where the compound is water soluble or the compound may be dispersed in a hydrophilic colloid solution using a latex or other polymers or using an oil/water emulsion type dispersion method, where the compound is not water-soluble. Examples of the oils which can be used for the oil/water emulsion type dispersion method, include oils for dissolving couplers used for oil protected type light-sensitive materials. Preferably, dispersion of the compound is made using oils for dissolving couplers used for oil protected type light-sensitive materials. For example, tri-o-cresyl phosphate, trihexyl phosphate, dioctyl butyl phosphate, dibutyl phthalate, diethyllaurylamide, 2,4-diallyl phenol and octyl benzoate, etc., can be used.

In order to disperse an oil phase containing the compound dissolved therein into an aqueous phase, a conventional surface active agent can be used. For example, an anionic surface active agent having an acid group such as a carboxylic acid group, a sulfonic acid group, phosphoric acid group, a sulfuric acid ester group or a phosphoric acid ester group, etc. and a nonionic, cationic or amphoteric surface active agent can be used.

Suitable hydrophilic colloids which can be used include materials known as photographic binders, such as gelatin examples of which include gelatin derivatives, a graft copolymer of gelatin with other high molecular weight materials, a cellulose derivative such as hydroxyethylcellulose, carboxymethylcellulose or cellulose sulfate, etc., sodium alginate, a starch derivative, various kinds of synthetic high molecular weight materials, such as a homo- or copolymer such as polyvinyl alcohol partial acetal, poly-N-vinylpyrrolidone, polyacrylic acid, polymethacrylic acid, polyacrylamide, polyvinylimidazole or polyvinyl pyrazole. In some cases, a latex may be employed. Examples of these binders include the compounds described in U.S. Pat. No. 3,518,088 and *Research Disclosure*, August 1976, No. 148-14850.

Further, it is possible to employ known photographic antioxidants or stabilizers in the emulsion. For example, a hydroquinone derivative, a reductone such as ascorbic acid, a hydroxylamine, a sulfonyl compound, an active methylene compound, etc. can be employed in the emulsion.

The coating amount of the precursor of the color developing agent used in the present invention is from 0.1 to 10 molar times and preferably from 0.25 to 5 molar times, the total amount of silver per unit area of the light-sensitive material. The precursor of the color developing agent may be incorporated into a light-sensitive layer containing a silver halide emulsion or into other layers (for example, an intermediate layer, a developing agent containing layer, a protective layer, a subbing layer, etc.), preferably in a silver halide emulsion layer.

The silver halide photographic light-sensitive material of the present invention may contain a 1-phenyl-3-pyrazolidone derivative in order to accelerate the development reaction. More specifically, the compounds as described, for example, in U.S. Pat. Nos. 2,751,297 and 3,902,905, Japanese Patent Application (OPI) Nos.

52422/78, 52055/80, 64339/81 and 40245/82, etc. may be used.

The silver halide photographic light-sensitive material of the present invention can be applied not only to a conventional color photographic light-sensitive material using three kinds of couplers, i.e., yellow, magenta and cyan couplers, but also a photographic light-sensitive material using a coupler capable of forming a black image upon color development.

The development processing method of the silver halide photographic light-sensitive material of the present invention can be the method comprising the three steps as described hereinbefore. Also it can be a method for forming an image comprising a dye and metalic silver in which a bleaching step (silver removing step) is omitted.

The development processing used in the present invention is the same as the conventional development processing except that the developing bath is an alkaline activator bath.

A suitable pH for the activator bath ranges from about 7 to 14 and particularly from about 8 to 13. A suitable temperature at which the activator bath can be used ranges from 20° to 70° C., but a preferred range is 30° to 60° C.

A suitable activator bath used in the present invention is a bath which is the same as a conventional developing solution (for example, a color developing solution) but which does not contain a color developing agent, a suitable buffer which can be used in the activator bath includes sodium hydroxide, potassium hydroxide, sodium carbonate, potassium carbonate, sodium tertiary phosphate, potassium tertiary phosphate, potassium metaborate and borax, etc., which may be used individually or as a combination thereof. Further, it is possible to use various salts such as disodium hydrogen phosphate, dipotassium hydrogen phosphate, sodium dihydrogen phosphate, potassium dihydrogen phosphate, sodium bicarbonate, potassium bicarbonate, boric acid, alkali metal nitrates or alkali metal sulfates, etc. in order to provide a buffering capability, for certain reasons of preparation or for the purpose of increasing the ionic strength.

Moreover, an antifogging agent can be incorporated into the activator bath in a suitable amount. Suitable antifogging agents include an inorganic halide compound and known organic antifogging agents. Typical examples of the inorganic halide compounds include a bromide such as sodium bromide, potassium bromide or ammonium bromide, etc. and an iodide such as potassium iodide or sodium iodide, etc. Examples of the organic antifogging agents include 6-nitrobenzindazole as described in U.S. Pat. No. 2,496,940, 5-nitrobenzimidazole as described in U.S. Pat. Nos. 2,497,917 and 2,656,271, diaminophenazine and o-phenylenediamine as described in *Nippon Shashingakkaishi*, vol. 11, page 48 (1948) and a heterocyclic compound such as mercaptobenzimidazole, methylbenzothiazole, mercaptobenzoxazole, thiouracil, 5-methylbenzotriazole or the compounds as described in Japanese Patent Publication No. 41675/71, etc. In addition, the antifogging agents as described in *Kagakushashin Binran*, vol. 2, page 119 Maruzen Co., (1959) may also be used.

In order to control surface layer development, the development restrainers described in Japanese Patent Publication Nos. 19039/71 and 6149/70 and U.S. Pat. No. 3,295,976, etc. can also be used.

In addition, if desired, ammonium chloride, potassium chloride or sodium chloride may be present in the activator bath. Further, if desired, a suitable development accelerator may be used in the bath. Examples of the development accelerators include a pyridinium compound as disclosed in U.S. Pat. No. 2,648,604, Japanese Patent Publication No. 9503/69 and U.S. Pat. No. 3,671,247 and other cationic compounds, a cationic dye such as phenosafranine, a neutral salt such as thallium nitrate or potassium nitrate, a nonionic compound such as polyethylene glycol or a derivative thereof or a polythioether, as described in Japanese Patent Publication No. 9504/69 and U.S. Pat. Nos. 2,533,990, 2,531,832, 2,950,970 and 2,577,127, an organic solvent and an organic amine as described in Japanese Patent Publication No. 9509/69 and Belgian Patent 682,862, ethanolamine, ethylenediamine and diethanolamine, etc. In addition, it is possible to use the development accelerators as described in detail in L. F. A. Mason, *Photographic Processing Chemistry*, pages 40–43, Focal Press, London (1966).

Further, benzyl alcohol and phenethyl alcohol as described in U.S. Pat. No. 2,304,925 and pyridine, ammonia, hydrazine and an amine as described in *Nippon Shashingakkaishi*, Vol. 14, page 74 (1952) can be used as an effective development accelerator in some cases.

Further, it is also possible to employ sodium sulfite, potassium sulfite, potassium bisulfite or sodium bisulfite in the activator bath.

Moreover, the activator bath may include a water softener, for example, a polyphosphoric acid compound such as sodium hexametaphosphate, sodium tetrapolyphosphate or sodium tripolyphosphate, or potassium salts of hexametaphosphoric acid, tetrapolyphosphoric acid or tripolyphosphoric acid, etc. and an aminopolycarboxylic acid such as ethylenediaminetetraacetic acid, nitrilotriacetic acid, cyclohexanediaminetetraacetic acid, iminodiacetic acid, N-(hydroxymethyl)ethylenediaminetriacetic acid or diethylenetriamine pentaacetic acid. Although the amount of the water-softener will vary depending on the hardness of the water used, generally from 0.5 to 10 g/liter is suitable. In addition to this, a calcium or magnesium sequestering agent may be used. Compounds of this type are described in detail in J. Willems *Belgisches Chemiches Industry*, Vol. 21, page 325 (1956) and ibid., Vol. 23, page 1105 (1958).

If desired, an organic solvent can also be employed in the activator bath.

Examples of suitable organic solvents include ethylene glycol, hexylene glycol, diethylene glycol, methyl cellosolve, methanol, ethanol, acetone, triethylene glycol, dimethylformamide, dimethylsulfoxide and the compounds as described in Japanese Patent Publication Nos. 33378/72 and 9509/69.

Although the amount of the organic solvent can vary over a wide range depending on the composition of the activator bath, a suitable amount is generally less than 50% by volume and usually less than 10% by volume of the solution used. However, it is possible to use an activator bath substantially not containing water.

An auxiliary developing agent such as N-methyl-p-aminophenol hemisulfate (Metol), benzyl-p-aminophenol hydrochloride, N,N-diethyl-p-aminophenol hydrochloride, p-aminophenol sulfate, phenidone and N,N,N',N'-tetramethyl-p-phenylenediamine hydrochloride, etc., can also be used. A preferred amount of the auxiliary developing agent is generally from 0.01 to 1.0 g/liter of the activator bath.

In addition, the following materials can also be employed, if necessary, in the activator bath.

For example, a competing coupler (non-color forming coupler) such as citrazinic acid, J-acid or H-acid, e.g., as described in Japanese Patent Publication Nos. 9505/69, 9506/69, 9507/69, 14036/70 and 9508/69, U.S. Pat. Nos. 2,742,832, 3,520,690, 3,560,212 and 3,645,737, etc. can be used.

A fogging agent such as an alkali metal borohydride, aminoborane or ethylenediamine, etc. as described in Japanese Patent Publication No. 38816/72 can be employed.

In color photographic light-sensitive materials wherein a compound which form a dye by reacting with an oxidized developing agent, the so-called coupler, is incorporated in a light-sensitive photographic emulsion layer, the precursor of a development agent used in the present invention may be added to the same layer or a different layer than the above described layer.

Such a structure is a particularly advantageous embodiment of the present invention. Such a color coupler has a chemical structure such that it does not diffuse into other layers during production or during processing.

An open chain diketomethylene type compound is widely used in general as a yellow coupler. Examples of suitable yellow couplers are described in, for example, U.S. Pat. Nos. 3,341,331, 2,875,057 and 3,551,155, German Patent Application (OLS) No. 1,547,868, U.S. Pat. Nos. 3,265,506, 3,582,322 and 3,725,072, German Patent Application (OLS) No. 2,162,899, U.S. Pat. Nos. 3,369,895 and 3,408,194 and German Patent Application (OLS) Nos. 2,057,941, 2,213,461, 2,219,917, 2,261,361 and 2,263,875, etc.

Although a 5-pyrazolone type compound is mainly used as a magenta coupler, an imidazolone type compound and a cyanoacetyl compound can also be used as a magenta coupler. Examples of suitable magenta couplers are described in, for example, U.S. Pat. Nos. 2,439,098, 2,600,788, 2,983,608, 3,062,653, 3,558,319, 3,582,322, 3,615,506, 3,519,429, 3,311,476, 3,419,391, 3,935,015 and 4,163,670, British Pat. Nos. 956,261 and 1,470,552, German Patent 1,810,464, and Japanese Patent Publication No. 2016/69, etc.

A phenol or naphthol derivative is mainly used as a cyan coupler. Examples of suitable cyan couplers include those described in U.S. Pat. Nos. 2,369,929, 3,560,212, 2,474,293, 2,698,794, 2,706,684, 2,895,826, 3,034,892, 3,311,476, 3,386,301, 3,458,315, 3,560,212, 3,582,322, 3,583,971 3,591,383, and 3,933,500, German Patent Application (OLS) No. 2,163,811, and Japanese Patent Publication No. 28836/70.

A resorcinol or m-aminophenol derivative is mainly used as a black image forming coupler. Examples of suitable black image forming couplers include those described in Japanese Patent Applications (OPI) No. 46029/78, 9924/79, and 172336/82.

Further, it is possible to incorporate a development inhibiting compound releasing type coupler (the so-called DIR coupler) or a compound which releases a development inhibiting compound during to color coupling reaction into the photographic material. Examples of suitable DIR couplers are described in U.S. Pat. Nos. 3,148,062, 3,227,554, 3,253,924, 3,617,291, 3,622,328 and 3,705,201, British Pat. No. 1,201,110 and U.S. Pat. Nos. 3,297,445, 3,379,529 and 3,639,417.

Two or more of the above described couplers, etc. can be employed in the same layer depending on the characteristics required for the light-sensitive material. Of course, the same compound may be employed in two or more different layers, if desired.

Preferably, the coupler is insoluble in water which is present in a coupler solvent (preferably, a coupler solvent having a suitable polarity). Typical useful coupler solvents are tri-o-cresyl phosphate, dibutyl phthalate, diethyl laurylamide, 2,4-diallylphenol and liquid dye stabilizers described as "improved photographic dye image stabilizing solvents" in *Product Licensing Index*, Vol. 83, pages 26–29 (March 1971).

Preferably the maximum absorption region of the cyan dye is in the range of about 600 to 680 nm, that of the magenta dye is in the range of about 500 to 580 nm and that of the yellow dye is in the range of about 400 to 480 nm.

The silver halide emulsion used in this invention can, in general, be produced by mixing a solution of a water soluble silver salt (for example, silver nitrate) with a solution of a water soluble halide (for example, potassium bromide) in the presence of a solution of a water soluble high molecular weight material such as gelatin. Not only silver chloride and silver bromide but also mixed silver halide such as silver chlorobromide, silver iodobromide or silver chloroiodobromide, etc. may be used as the silver halide.

The grains of the silver halide may have any shape such as a cubic form, an octahedral form and a mixed crystal form thereof.

The grains of the silver halide can be produced using known conventional methods, such as by the so-called single or double jet process or the controlled double jet prcess.

Suitable photographic emulsions are described in C. E. K. Mees, *The Theory of the Photographic Process*, MacMillan Co. New York (1966) and P. Glafkides, *Chimie Photographique*, Paul Montel, Paris (1957) and they can be prepared by an ammonia method, a neutral method or an acid method.

After formation of the silver halide grains, the grains are washed with water to remove by-produced water soluble salts (for example, potassium nitrate in the case of producing silver bromide using silver nitrate and potassium bromide) from the system, and they are then heated in the presence of a chemical sensitizing agent (for example, sodium thiosulfate, N,N,N'-trimethylthiourea, a monovalent gold-thiocyanate complex salt, a thiosulfate complex salt, stannous chloride and hexamethylenetetramine, etc.) to increase the sensitivity without increasing the grain size. Such processes are generally described in Mees, supra and Glafkides, supra.

The above-described silver halide emulsion may be chemically sensitized using conventional techniques. Examples of suitable chemical sensitizing agents which can be used include a gold compound (for example, chloroaurate or gold trichloride) as described in U.S. Pat. Nos. 2,399,083, 2,540,085, 2,597,856 and 2,597,915, a salt of a noble metal (for example, platinum, palladium, iridium, rhodium or ruthenium, etc.) as described in U.S. Pat. Nos. 2,448,060, 2,540,086, 2,566,245, 2,566,263 and 2,598,079, a sulfur compound which forms silver sulfide by reacting with a silver salt, as described in U.S. Pat. Nos. 1,574,944, 2,410,689, 3,189,458 and 3,501,313, and a reducing agent (for example, a stannous salt and an amine, etc.) as described in U.S. Pat. Nos. 2,487,850, 2,518,698, 2,521,925, 2,521,926, 2,694,637, 2,983,610 and 3,201,254, etc.

An antifogging agent for silver halide may be added to the light-sensitive layer of the photographic light-sensitive material of the present invention. Typical antifogging agents which can be used are a heterocyclic organic compound such as a tetrazole, an azaindene or a triazole, etc. and an aromatic or heterocyclic compound having a mercapto group.

The layer of the photographic light-sensitive material of the present invention may contain a hardening agent, a plasticizer, a lubricating agent, a surface active agent, a lustering agent and other additives commonly used in the photographic field.

Examples of hydrophilic colloids which can be used include gelatin, colloidal albumin, casein, a cellulose derivative such as carboxymethyl cellulose or hydroxyethyl cellulose, etc., a saccharide derivative such as agar, sodium alginate or a starch derivative, etc. and a synthetic hydrophilic colloid such as polyvinyl alcohol, poly-N-vinylpyrrolidone, an acrylic acid copolymer, polyacrylamide, a derivative thereof or a partially hydrolyzed product thereof, etc. If desired, a compatible mixture of two or more of these colloids can be used. Of these colloids, although gelatin is the most generally used, a part or all of the gelatin may be replaced by not only a synthetic high molecular material but also by a gelatin derivative, namely, a material modified by treating gelatin with a compound having one group capable of reacting with an amino group, an imino group, a hydroxy group or a carboxyl group as a functional group in the gelatin molecule, or a graft polymer obtained by grafting the chain of other high molecular weight materials onto gelatin.

The photographic emulsion may be, if desired, spectrally sensitized or supersensitized using one or more cyanine dyes such as a cyanine, merocyanine or hemicyanine dye, etc. or using cyanine dyes together with a styryl dye. These spectral sensitization techniques are known and are described in, for example, U.S. Pat. Nos. 2,493,748, 2,519,001, 2,977,229, 3,480,434, 3,672,897, 3,703,377, 2,688,545, 2,912,329, 3,397,060, 3,615,635 and 3,628,964, British Pat. Nos. 1,195,302, 1,242,588 and 1,293,862, West German Patent Application (OLS) Nos. 2,030,326 and 2,121,780, Japanese Patent Publication Nos. 4936/68, 14030/69 and 10773/68, U.S. Pat. Nos. 3,511,664, 3,522,052, 3,527,641, 3,615,613, 3,615,632, 3,617,295, 3,635,721 and 3,694,217 and British Pat. Nos. 1,137,580 and 1,216,203, etc. Suitable dyes can be selected depending on the purpose or use of the light-sensitive material, such as the wavelength range to be sensitized or the sensitivity desired, etc.

These photographic emulsions are applied to a planar material which does not undergo a marked dimensional change during processing, for example, a rigid support such as glass, metal or porcelain or a flexible support, depending on the end-use. Typical examples of flexible supports, are a cellulose nitrate film, a cellulose film, a cellulose acetate butyrate film, a cellulose acetate propionate film, a polystyrene film, a polyethylene terephthalate film, a polycarbonate film and a laminate of these resins, a thin glass film and paper, etc. which are used usually for photographic light-sensitive materials. Good results are also obtained using paper coated or laminated with baryta or an α-olefin polymer, particularly, a polymer of an α-olefin having from 2 to 10 carbon atoms, such as polyethylene, polypropylene or a ethylene-butene copolymer, etc., and a plastic film the surface of which has been roughened as described in Japanese Patent Publication No. 19068/72 to improve adhesiveness to other high molecular weight materials and to improve printability.

A transparent support or an opaque support can be selected from the above-described supports depending on the use of the light-sensitive material. As a transparent support, not only a colorless transparent support but also a colored transparent support obtained by adding dyes or pigments to a transparent support may be used. Use of a colored transparent support for X-ray films is described in *J. SMPTE*, Vol. 67, page 296 (1958).

Examples of opaque supports which can be used include not only an intrinsically opaque support such as paper but also a film obtained by adding dyes or pigments such as titanium oxide to a transparent film, a plastic film the surface of which has been processed in the manner described in Japanese Patent Publication No. 19068/72 and paper or a plastic film to which carbon black or dyes have been added to render it completely light shielding. Where the adhesive strength between the support and the photographic emulsion layer is insufficient, a layer which is adhesive to both of the support and the emulsion layer is employed as a subbing layer. Further, in order to further improve the adhesive property, the surface of the support may be subjected to a preliminary treatment such as a corona discharge treatment, an ultraviolet light treatment or flame treatment, etc.

As described above, the photographic light-sensitive material used in the present invention comprises a support and a dye image providing unit layer on the support. A multilayer color photographic light-sensitive material for providing multicolor images has at least two dye image providing unit layers wherein each layer first records light having a certain wavelength range. The unit layers contain a light-sensitive silver salt which is generally sensitive to light having a certain wavelength range and is usually combined with a photographic coupler. In order to prevent the occurrence of any color mixing between the dye image providing unit layers, the unit layers are effectively separated by a barrier layer, an intermediate layer, a layer containing an agent for removing the oxidation product of a developing agent or another layer. Methods of effectively separating the unit layers are known in the photographic field and have been utilized in many commercial color light-sensitive materials. Further, a light-sensitive material having a layer for preventing development contamination as described in U.S. Pat. Nos. 3,737,317, 3,892,572 and 3,984,245 can be used for the present invention.

The present invention provides excellent advantages as compared with the prior methods. Some of these advantages are described below.

First, less fogging occurs.

Second, a residual color is not formed on the processed light-sensitive material, because the precursor used in the present invention is colorless after processing with the activator bath.

Third, unprocessed light-sensitive material has good stability with the lapse of time.

The present invention will be explained in greater detail with reference to the following examples, but the present invention should not be construed as being limited thereto.

EXAMPLE 1

A multilayer color paper photographic light-sensitive material was prepared by coating layers having the compositions shown below on a paper support laminated with polyethylene.

Layer-1: Developing agent containing layer

Compound (4) according to the present invention was dispersed using dibutyl phthalate and ethyl acetate and coated at a coating amount of 2.7 g/m².

| Gelatin | 4.0 g/m² |
| Dibutyl phthalate | 750 mg/m² |
| Ethyl acetate | 750 mg/m² |
| Hardening agent | 40 mg/m² |

Layer-2: Intermediate Layer

| Gelatin | 1.0 g/m² |

Layer-3: Blue-sensitive silver halide emulsion layer

Yellow coupler (Y-1) dissolved in dioctyl butyl phosphate was dispersed in a silver chlorobromide (bromide: 80 mol%) emulsion and coated.

| Silver | 0.4 g/m² |
| Coupler | $8 \times 10^{-4}$ mol/m² |
| Gelatin | 1.5 g/m² |
| Oil | 0.3 g/m² |
| Hardening agent | 15 mg/m² |

Layer-4: Intermediate layer

| Gelatin | 1.0 g/m² |

Layer-5: Green-sensitive silver halide emulsion layer

Magenta coupler (M-1) dissolved in tricresyl phosphate was dispersed in a silver chlorobromide (bromide: 60 mol%) emulsion and coated.

| Silver | 0.4 g/m² |
| Coupler | $5.8 \times 10^{-4}$ mol/m² |
| Gelatin | 1.5 g/m² |
| Oil | 0.35 g/m² |
| Hardening agent | 15 mg/m² |

Layer-6: Intermediate layer 2-(2-Hydroxy-3-sec-butyl-5-tert-butylphenyl)benzotriazole dissolved in dibutyl phthalate was dispersed and coated.

| Gelatin | 1.2 g/m² |
| Oil | 0.25 g/m² |
| Benzotriazole (described above) | 1.0 g/m² |
| Hardening agent | 12 mg/m² |

Layer-7: Red-sensitive silver halide emulsion layer

Cyan coupler (C-1) dissolved in dibutyl phthalate was dispersed in a silver chlorobromide (bromide: 50 mol%) emulsion and coated.

| Silver | 0.3 g/m² |
| Coupler | $8.5 \times 10^{-4}$ mol/m² |
| Gelatin | 1.5 g/m² |
| Oil | 0.2 g/m² |
| Hardening agent | 15 mg/m² |

Layer-8: Protective layer

| Gelatin | 1 g/m² |

The compounds used had the following formulae.

Hardening agent

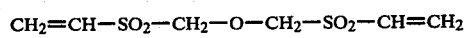

Yellow coupler (Y-1)

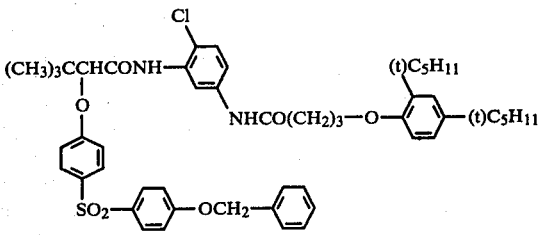

Magenta coupler (M-1)

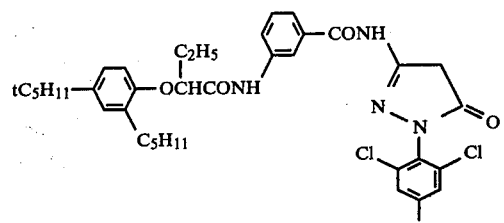

Cyan coupler (C-1)

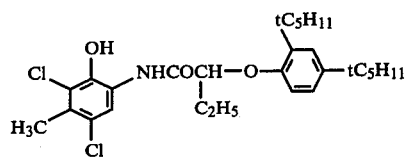

The photographic material thus prepared was designated Sample 1.

Sample 2 and 3 were prepared in the same manner as described in Sample 1 except that 1.5 g/m² of Compound A having the structure shown below and 2.0 g/m² of Compound B described below were used in place of Compound (4) in Layer-1 of Sample 1, respectively.

Compound A

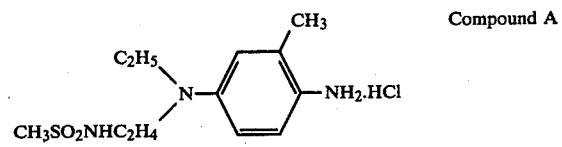

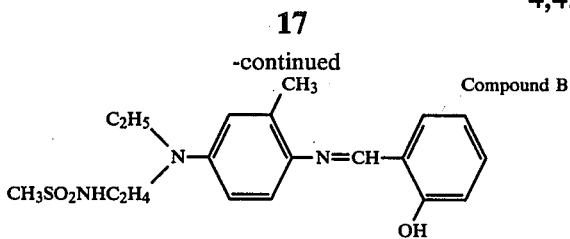

Compound B

Samples 1, 2 and 3 were exposed to light through a step wedge and subjected to the following processing.

| Processing Step | Temperature | Time |
|---|---|---|
| Activator Development | 38° C. | 2 min |
| Bleach-Fixing | 38° C. | 1 min |
| Washing with water | 38° C. | 2 min |
| Drying | 70° C. | 2 min |

The processing solutions used had the following compositions.

| Activator Solution | |
|---|---|
| Benzyl Alcohol | 15 ml |
| Sodium Sulfite | 1.5 g |
| Potassium Bromide | 0.6 g |
| Sodium Carbonate (monohydrate) | 30 g |
| Water to make | 1 liter |
| | (pH was adjusted to 10.0) |

| Bleach-Fixing Solution | |
|---|---|
| Ammonium Thiosulfate | 130 g |
| Sodium Metabisulfite | 14 g |
| Sodium Sulfite (anhydrous) | 3 g |
| Ammonium Fe (III) Ethylenediaminetetraacetate | 65 g |
| Water to make | 1 liter |
| | (pH was adjusted to 6.7 to 6.8) |

The maximum density and the fog density of the samples thus processed were measured using a Macbeth densitometer. The results obtained are shown in Table 1 below.

TABLE 1

| | | Fog Density | | | Maximum Density | | |
|---|---|---|---|---|---|---|---|
| Sample No. | | Y | M | C | Y | M | C |
| 1 | (Present Invention) | 0.18 | 0.22 | 0.20 | 1.92 | 2.05 | 2.01 |
| 2 | (Comparison) | 0.45 | 0.30 | 0.25 | 2.50 | 2.84 | 2.60 |
| 3 | (Comparison) | 0.30 | 0.22 | 0.20 | 1.20 | 1.35 | 1.08 |

It is apparent from the results shown in Table 1 above that in Sample 1 according to the present invention, the fog density is maintained at a low level and sufficiently high maximum density is obtained. On the contrary, Sample 2 results in high fog density and is poor in the stability of the light-sensitive material with the lapse of time, and Sample 3 has relatively low fog density but insufficient maximum density.

EXAMPLE 2

1.2 g of 2', 6'-dihydroxyundecanophenone, that is, a black color forming coupler as described in Japanese Patent Application (OPI) No. 172336/82 and 1.2 g of Compound (1) according to the present invention as a precursor of a developing agent was dissolved at 40° C. in a mixture solution of 1.5 ml of dibutyl phthalate and 2.5 ml of ethyl acetate. The solution was mixed with a 10% aqueous gelatin solution, to which was added 0.05 g of sodium alkylbenzenesulfonate and the mixture was dispersed using a homogenizer. To the dispersion thus prepared was added 5 ml of a 10% aqueous gelatin solution containing 0.2 g of 4-hydroxymethyl-4-methyl-1-phenyl-3-pyrazolidinone and 0.05 g of ascorbic acid whereby the coupler dispersion containing the precursor of a developing agent was prepared. The coupler dispersion was mixed with a silver iodobromide (particle size: 1.2μ, iodide: 2 mol%) emulsion and the mixture was coated on a transparent polyethylene terephthalate support to prepare a sample. The coating amounts of silver and Compound (1) in this sample were 2 g/m² and 2.6 g/m², respectively. This sample was designated Sample 4.

Sample 5 was prepared in the same manner as described in Sample 4 except that 0.65 g of Compound A having the structure shown below was used in place of the precursor of a developing agent in Sample 4.

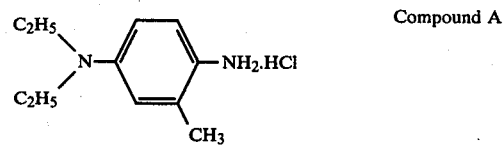

Compound A

Also, Sample 6 was prepared in the same manner as described in Sample 5 except using 0.87 g of Compound B having the structure shown below in place of Compound A.

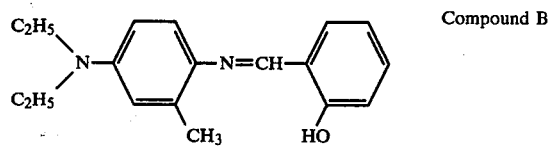

Compound B (described in U.S. Pat. No. 3,342,599)

Further, Sample 7 was prepared in the same manner as described in Sample 5 except using 1.33 g of Compound C having the structure shown below in place of Compound A.

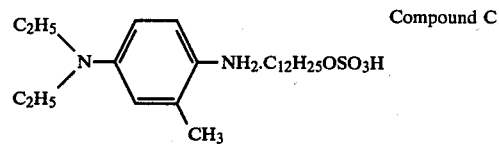

Compound C (described in Japanese Patent Application (OPI) No. 16133/81)

Samples 4, 5, 6 and 7 were exposed to light through a step wedge and subjected to the following processing.

| Processing Step | Temperature | Time |
|---|---|---|
| Activator Development | 35° C. | 25 sec. |
| Fixing | 35° C. | 25 sec. |
| Washing with Water | 33° C. | 20 sec. |

The processing solutions used had the following compositions.

| Activator Solution | |
|---|---|
| Benzyl Alcohol | 10 ml |
| Potassium Bromide | 5 g |
| 5-Methylbenzotriazole | 0.05 g |
| Sodium Hydroxide | 10 g |
| Water to make | 1 liter |
| | (pH was about 13.2 at 25° C.) |

| Fixing Solution | |
|---|---|
| Ammonium Thiosulfate | 175 g |
| Sodium Sulfite (anhydrous) | 15 g |
| Glacial Acetic Acid | 12 ml |
| Sodium Metaborate | 15 g |
| Potassium Alum | 20 g |
| Water to make | 1 liter |

The results obtained are shown in Table 2 below.

Furthermore, Samples 4, 5, 6 and 7 were subjected to a accelerated ageing test under the condition of 50° C. and 70% RH for 3 days and then exposed to light and processed in the same manner as described above. The results obtained are also shown in Table 2 below.

TABLE 2

| Sample No. | | Compound | Fog | Maximum Density | Relative Sensitivity |
|---|---|---|---|---|---|
| 1 | (Present Invention) | (1) | 0.24 | 1.95 | 100 |
| 2 | (Comparison) | A | 0.51 | 2.31 | 88 |
| 3 | (Comparison) | B | 0.21 | 0.95 | 30 |
| 4 | (Comparison) | C | 0.63 | 2.12 | 75 |
| [After Accelerated Ageing Test] | | | | | |
| 1 | (Present Invention) | (1) | 0.29 | 1.82 | 73 |
| 2 | (Comparison) | A | 0.95 | 1.91 | 64 |
| 3 | (Comparison) | B | 0.40 | 1.12 | 27 |
| 4 | (Comparison) | C | 1.05 | 1.76 | 54 |

It is apparent from the results shown in Table 2 above that Compound B for comparison has a low maximum density while having a low level of fog and thus it can not be practically employed. On the other hand, Compound A and C for comparison show high maximum densities with high fog densities which are particularly remarkable after the accelerated ageing test. On the contrary, the compound according to the present invention provides sufficiently high maximum density and a low level of fog and these properties are only changed to a small extent after the accelerated ageing test. Therefore, it is understood that the compound according to the present invention has extremely good properties as a precursor of a color developing agent.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material, comprising a support having provided thereon a diffusion resistant coupler, a light-sensitive silver halide and a compound represented by the following general formula (I)

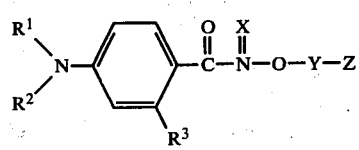

wherein $R^1$ and $R^2$ independently represent an alkyl group having from 1 to 5 carbon atoms, a hydroxyalkyl group having from 1 to 5 carbon atoms, an alkoxyalkyl group having from 2 to 10 carbon atoms or an alkylsulfonamidoalkyl group having from 2 to 10 carbon atoms; $R^3$ represents a hydrogen atom, an alkyl group having from 1 to 5 carbon atoms or an alkoxy group having from 1 to 5 carbon atoms; X represents a hydrogen atom or a group capable of being removed with alkali; Y represents

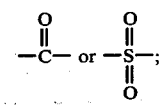

and Z represents an alkyl group, an alkenyl group, an aryl group or a heterocyclic group.

2. A silver halide photographic light-sensitive material as claimed in claim 1, wherein X represents an alkylcarbonyl group or

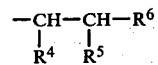

wherein $R^4$ and $R^5$ independently represent a hydrogen atom or an alkyl group; and $R^6$ represents an electron withdrawing group.

3. A silver halide photographic light-sensitive material as claimed in claim 1 wherein Z represents an alkyl group having from 1 to 10 carbon atoms, an alkenyl group having from 2 to 10 carbon atoms, an aryl group having from 6 to 10 carbon atoms or a heterocyclic group having from 1 to 10 carbon atoms.

4. A silver halide photographic light-sensitive material as claimed in claim 1, wherein $R^2$ and $R^3$ independently represent an alkyl group having from 1 to 5 carbon atoms.

5. A silver halide photographic light-sensitive material as claimed in claim 1, wherein Y represents

6. A silver halide photographic light-sensitive material as claimed in claim 1, wherein Z represents a substituted or unsubstituted alkyl group or a substituted or unsubstituted aryl group.

7. A silver halide photographic light-sensitive material as claimed in claim 1, wherein Z represents a substituted or unsubstituted dihydroxybenzene, a substituted or unsubstituted dihydroxynaphthalene, a substituted or unsubstituted aminophenol or a substituted or unsubstituted aminonaphthol.

8. A silver halide photographic light-sensitive material as claimed in claim 1, wherein the compound represented by the general formula (I) is present in the photographic light-sensitive material in an amount of from 0.1 to 10 molar times the total amount of silver per unit area of the photographic light-sensitive material.

9. A silver halide photographic light-sensitive material as claimed in claim 1, wherein the compound represented by the general formula (I) is present in the photographic light-sensitive material in an amount of from 0.25 to 5 molar times the total amount of silver per unit area of the photographic light-sensitive material.

10. A silver halide photographic light-sensitive material as claimed in claim 1, wherein the compound represented by the general formula (I) is present in a layer selected from the group consisting of a light-sensitive layer, an intermediate layer, a developing agent containing layer, a protective layer or a subbing layer.

11. A silver halide photographic light-sensitive material as claimed in claim 1, wherein the compound represented by the general formula (I) is present in a light-sensitive layer containing the light-sensitive silver halide and the diffusion resistant coupler.

12. A silver halide photographic light-sensitive material as claimed in claim 1, further comprising an additional layer selected from the group consisting of an intermediate layer, a developing agent containing layer, a protective layer and a subbing layer wherein the compound represented by the general formula (I) is present within an additional layer.

13. A silver halide photographic light-sensitive material as claimed in claim 1, wherein the diffusion resistant coupler is selected from the group consisting of a yellow dye forming coupler, a magenta dye forming coupler, a cyan dye forming coupler and a black dye forming coupler.

14. A silver halide photographic light-sensitive material as claimed in claim 1, wherein Z is selected from the group consisting of an alkyl containing 1 to 10 carbon atoms, an alkenyl group containing 2 to 10 carbon atoms, an aryl group containing 6 to 10 carbon atoms, and heterocyclic group containing 1 to 10 carbon atoms.

15. A silver halide photographic light-sensitive material as claimed in claim 1, wherein the compound represented by the general formula (I) is a compound selected from the group consisting of:

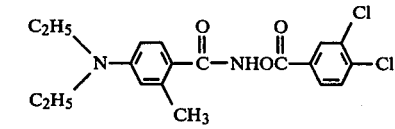
(1)

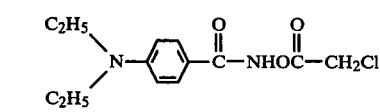
(2)

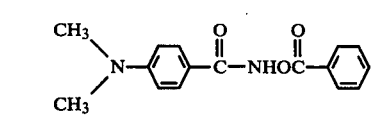
(3)

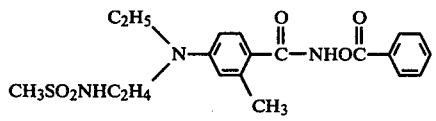
(4)

-continued

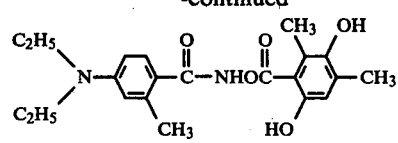
(5)

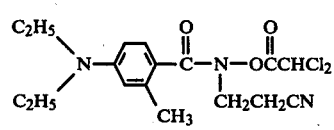
(6)

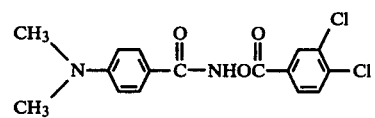
(7)

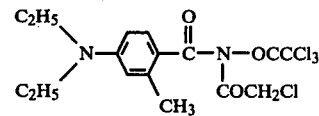
(8)

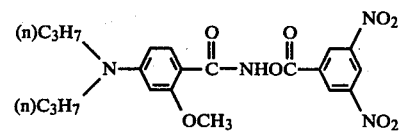
(9)

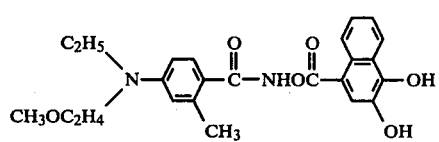
(10)

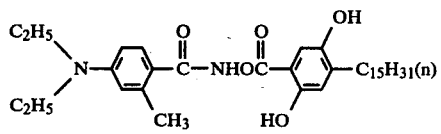
(11)

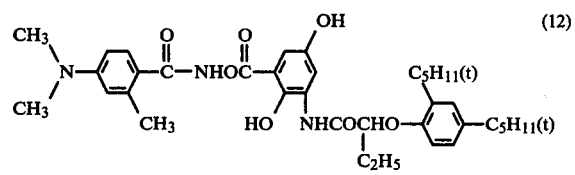
(12)

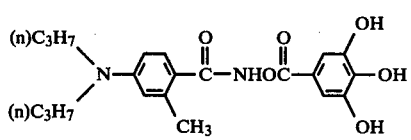
(13)

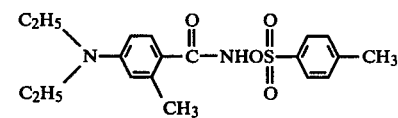
(14)

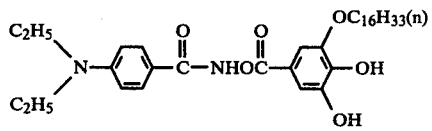
(15)

-continued

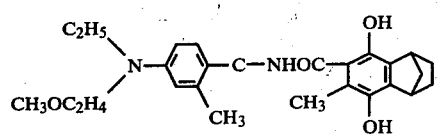

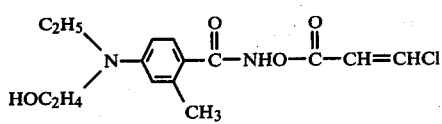

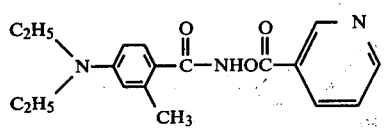

wherein said compound is present in the material in an amount of from 0.25 to 5 molar times the total amount of silver per unit area of the photographic material.

16. A method for forming a photographic image, comprising the steps of:

providing a silver halide photographic light-sensitive material comprised of a support having thereon a diffusion resistant coupler, a light-sensitive silver halide and a compound represented by the general formula (I):

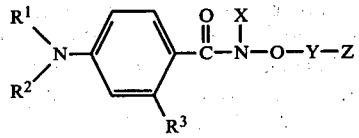

wherein $R^1$ and $R^2$ independently represent an alkyl group having from 1 to 5 carbon atoms, an hydroxyalkyl group having from 1 to 5 carbon atoms, an alkoxyalkyl group having from 2 to 10 carbon atoms or an alkylsulfonamidoalkyl group having from 2 to 10 carbon atoms;

$R_3$ represents a hydrogen atom, an alkyl group having from 1 to 5 carbon atoms or an alkoxy group having from 1 to 5 carbon atoms; X represents a hydrogen atom or a group capable of being removed with alkali; Y represents

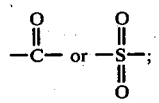

and Z represents an alkyl group, an alkenyl group, an aryl group or a heterocyclic group;

imagewise exposing the silver halide photographic light-sensitive material; and developing the imagewise exposed material with an activator solution comprising an aqueous alkaline processing solution having a pH within a range of 7 to 14.

17. A method for forming a photographic image as claimed in claim 16, further comprising the step of subjecting the developed photographic material to a bleaching process to remove developed silver formed during the developing step.

18. A method for forming a photographic image as claimed in claim 16, further comprising the step of subjecting the developed photographic material to a fixing process without removing developed silver.

* * * * *